US011123879B2

(12) United States Patent
Fukaya

(10) Patent No.: US 11,123,879 B2
(45) Date of Patent: Sep. 21, 2021

(54) FINGER MECHANISM AND HUMANOID HAND INCORPORATING SAME FINGER MECHANISM

(71) Applicant: Preferred Networks, Inc., Tokyo (JP)

(72) Inventor: Naoki Fukaya, Tokyo (JP)

(73) Assignee: Preferred Networks, Inc., Tokyo (JP)

( * ) Notice: Subject to any disclaimer, the term of this patent is extended or adjusted under 35 U.S.C. 154(b) by 47 days.

(21) Appl. No.: 16/498,926

(22) PCT Filed: Mar. 20, 2018

(86) PCT No.: PCT/JP2018/011060
§ 371 (c)(1),
(2) Date: Dec. 23, 2019

(87) PCT Pub. No.: WO2018/180782
PCT Pub. Date: Oct. 4, 2018

(65) Prior Publication Data
US 2020/0206950 A1    Jul. 2, 2020

(30) Foreign Application Priority Data
Mar. 30, 2017   (JP) .............................. JP2017-068020

(51) Int. Cl.
*B25J 15/00*   (2006.01)
*B25J 15/10*   (2006.01)
(Continued)

(52) U.S. Cl.
CPC ....... *B25J 15/0009* (2013.01); *B25J 15/0226* (2013.01); *A61F 2/586* (2013.01)

(58) Field of Classification Search
CPC ..... B25J 15/0009; B25J 15/0226; A61F 2/586
(Continued)

(56) References Cited

U.S. PATENT DOCUMENTS 2,567,066 A * 9/1951 Goldman .................. A61F 2/60
                                                            623/24
2,598,593 A * 5/1952 Parker ..................... A61F 2/586
                                                            623/64
(Continued)

FOREIGN PATENT DOCUMENTS

JP           4-46787 A    2/1992
JP       2009-101453 A    5/2009
(Continued)

*Primary Examiner* — Paul T Chin
(74) *Attorney, Agent, or Firm* — Westerman, Hattori, Daniels & Adrian, LLP

(57) ABSTRACT

A finger mechanism for a robot, an artificial hand, and the like, wherein a fourth bone member (14) of the bone members of the finger mechanism and corresponding to the distal phalanx comprises: a support portion (15) that is rotatably coupled to a third bone member corresponding to the middle phalanx by a rotational shaft (g5); and a nail portion (16). The nail portion (16) can freely rotate about a shaft (g7) at a right angle or a near right angle to the rotational shaft (g5), and a return mechanism (17) to return the rotated nail portion (16) to a reference position is provided between the support portion (15) and the nail portion (16). In this manner, in response to the amount of force applied to the fourth bone member (14), it is possible for only the nail portion (16) to rotate in a direction to easily grasp an object to be held.

20 Claims, 9 Drawing Sheets

(51) Int. Cl.
*B25J 15/02* (2006.01)
*A61F 2/58* (2006.01)

(58) Field of Classification Search
USPC .......... 294/106, 111, 119.1, 907; 901/31, 36
See application file for complete search history.

(56) References Cited

U.S. PATENT DOCUMENTS

| | | | | |
|---|---|---|---|---|
| 4,946,380 A * | 8/1990 | Lee | ...................... | B25J 15/0009 |
| | | | | 623/24 |
| 5,378,033 A * | 1/1995 | Guo | ........................ | A61F 2/583 |
| | | | | 294/116 |
| 5,647,723 A * | 7/1997 | Rush | ...................... | B25J 9/1085 |
| | | | | 294/111 |
| 7,556,299 B2 * | 7/2009 | Koyama | .............. | B25J 15/0009 |
| | | | | 294/106 |
| 8,573,663 B1 * | 11/2013 | Lin | ...................... | B25J 15/0009 |
| | | | | 294/111 |
| 2007/0040400 A1 * | 2/2007 | Greenhill | ............. | B25J 15/0009 |
| | | | | 294/106 |
| 2007/0063526 A1 * | 3/2007 | Poudrier | ................. | B60P 1/286 |
| | | | | 296/39.3 |
| 2012/0109337 A1 * | 5/2012 | Schulz | .................... | A61F 2/586 |
| | | | | 623/64 |
| 2012/0330432 A1 * | 12/2012 | Fong | ....................... | A61F 2/586 |
| | | | | 623/21.15 |
| 2014/0303750 A1 * | 10/2014 | MacDuff | ................. | A61F 2/586 |
| | | | | 623/57 |
| 2015/0021949 A1 * | 1/2015 | Schuster | ............. | B25J 15/0028 |
| | | | | 294/207 |
| 2015/0230941 A1 | 8/2015 | Jury | | |

FOREIGN PATENT DOCUMENTS

| | | |
|---|---|---|
| JP | 4462742 B2 | 5/2010 |
| JP | 2010-264548 A | 11/2010 |
| JP | 2011-62788 A | 3/2011 |
| JP | 2013-240863 A | 12/2013 |
| JP | 2015-54354 A | 3/2015 |
| WO | 2014/027897 A1 | 2/2014 |
| WO | 2016/141266 A1 | 9/2016 |

* cited by examiner

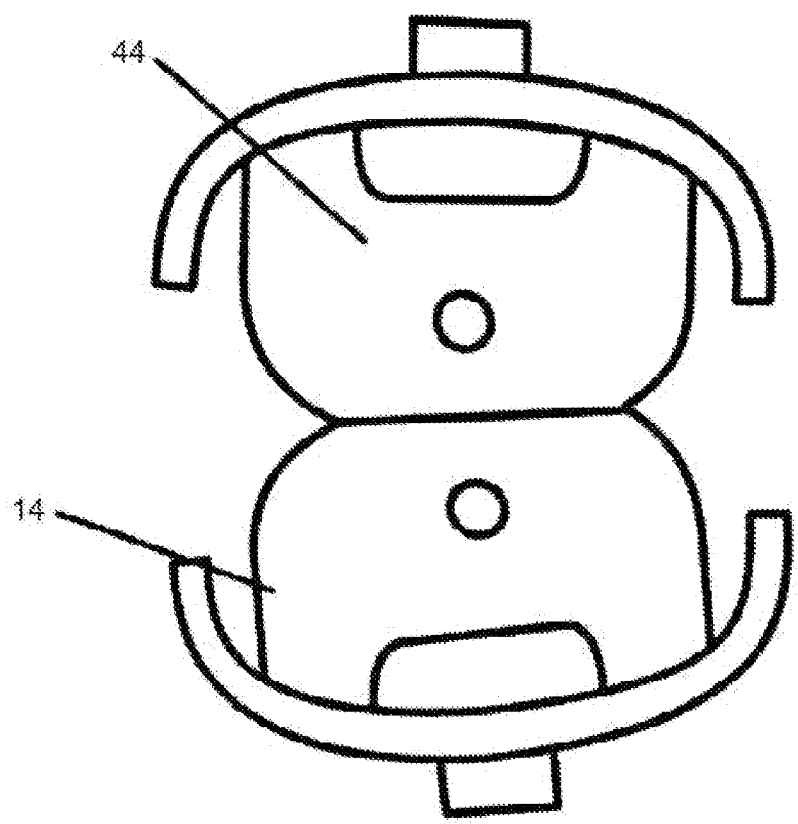

FINGER MECHANISM AND HUMANOID HAND INCORPORATING SAME FINGER MECHANISM

TECHNICAL FIELD

The present invention relates to a finger mechanism used by being attached to an arm tip of a robot or used as a prosthetic hand of a disabled person, or the like, and also relates to a humanoid hand incorporating the finger mechanism, such as a humanoid hand capable of delicate tasks using fingertips.

BACKGROUND ART

In a human hand, the tip of the thumb can touch the tips of the other fingers. A humanoid hand capable of such movement is disclosed in PTL 1 and PTL 2.

PTL 1 was proposed by the inventors of the present invention and has a structure in which three finger plates respectively corresponding to the proximal phalanxes, the intermediate phalanxes, and the distal phalanxes of a human are rotatably connected at end portions thereof, link mechanisms including rotating plates and drive rods are arranged along these finger plates, and the rotating plates, the drive rods, and the finger plates are pivotally attached in a rotatable manner.

According to PTL 1, a group of links in which a plurality of link plates are arranged in a reverse tournament form on one stepping motor are connected, and the stepping motor is driven to cause the drive rods connected to the distal ends of the links to perform a pulling movement, thereby rotating each of the finger plates via the link mechanisms linked to this pulling movement. By optimally setting the link mechanisms, the tip of the thumb and the tip of each of the other fingers can be brought into contact with each other.

PTL 2 proposes a humanoid hand in which slave fluid pressure cylinders are disposed respectively at the sections corresponding to the proximal phalanxes and the intermediate phalanxes in order to cause the parts corresponding to the intermediate phalanxes and the distal phalanxes of a human to rotate, and a humanoid hand in which a force sensor for detecting a force acting on a fingertip portion is disposed at an IP joint.

According to PTL 2, the slave fluid pressure cylinders are disposed at two sections of each of the fingers, including the thumb, so it is considered possible to design a humanoid hand in such a manner that the tip of the thumb and the tip of each of the other fingers are brought into contact with each other.

CITATION LIST

Patent Literature

[PTL 1] Japanese Patent No. 4462742
[PTL 2] Japanese Patent Application Laid-open No. 2010-264548

SUMMARY OF INVENTION

Technical Problem

Unfortunately, according to the patent literature described above, both delicate tasks and rough tasks such as grasping heavy objects that humans do cannot be achieved; especially delicate tasks cannot be realized.

When fingertips are brought into gentle contact with each other without pressure, the fingertips are not parallel to each other and are in partial contact, almost in point contact. The fingertips are in such a state when the person carries out extremely delicate tasks such as twisting paper threads, grasping a light, fragile object, and threading a needle. On the other hand, when the fingertips are pressed against each other somewhat strongly in order to grasp a heavy, hard object or the like, the fingertips rotate, increasing the area of contact therebetween.

Especially when the person carries out a delicate, complicated task, the state shown in FIG. 8 and the state shown in FIG. 9 are repeatedly executed alternately, and humanoid hands capable of performing such movements have not been contrived yet.

An object of the present invention, therefore, is to provide a finger mechanism and a humanoid hand that are capable of performing both delicate tasks and rough tasks such as grasping heavy objects that humans do. Specifically, an object of the present invention is to realize a structure in which, when the contact pressure between the tip of the thumb and another fingertip (e.g., the second finger) is small, these fingertips are brought into partial contact to obtain a small area of contact and the contact surfaces of these fingertips become parallel to each other and consequently the area of contact increases as the contact pressure increases.

Solution to Problem

As a result of intensive studies by the inventors of the present invention in order to achieve the foregoing object, the inventors of the present invention have found, in the process of developing a humanoid hand, that partial contact between the fingertips and contact therebetween with a large area of contact as described above are more likely to be repeated frequently when the thumb and the second finger (index finger) come into contact with each other. Based on this finding, the inventors of the present invention investigated the mechanism and completed the present invention. In other words, the finger mechanism according to the present invention is a finger mechanism for a robot or a prosthetic hand, wherein a fourth bone member corresponding to a distal phalanx out of bone members of the finger mechanism is constituted by a support portion and a nail portion, the support portion being connected to a third bone member corresponding to an intermediate phalanx and the nail portion being attached so as to be rotatable with respect to the support portion, about an axis perpendicular or nearly perpendicular to a rotational axis about which the support portion is rotatable with respect to the third bone member, and a return mechanism for returning the rotated nail portion to a reference position is provided between the support portion and the nail portion.

The description "perpendicular or nearly perpendicular" means that the angle of the axis about which the nail portion rotates is perpendicular or nearly perpendicular with respect to the pivot axis of the support portion and the third bone member, and, specifically in the preferable range of 90°±20°.

According to the present invention, two-degree-of-freedom may be provided to the joint portion between the fourth bone member corresponding to the distal phalanx and the third bone member, to obtain the effect in which the fourth bone member (or the nail portion) can freely rotate about the axis perpendicular or nearly perpendicular to the rotational axis about which the fourth bone member can rotate with the third bone member with respect to the support portion. The description "perpendicular or nearly perpendicular" means the same thing described above and is preferably in the range of 90°±20°. The same meaning applies to the description "perpendicular or nearly perpendicular" below.

By providing the portion corresponding to a DIP joint of a finger with two-degree-of-freedom as described above to create a so-called two-degree-of-freedom control system, the nail portion can be rotated freely about the axis perpendicular or nearly perpendicular to the pivot axis of the third bone member and the fourth bone member.

As will be described hereinafter, two directions obtained when providing two-degree-of-freedom preferably mean two separate directions that are perpendicular to each other.

The present invention may be configured to achieve the effect in which only a fingertip portion of the fourth bone member coming into contact with an object is rotatable about the axis perpendicular or nearly perpendicular to the rotational axis about which the fourth bone member can rotate with the third bone member with respect to the support member.

The fingertip portion means a part corresponding to a fingertip including the nail portion.

Either the support portion or the nail portion may be provided with a stopper for restricting a rotation range of the nail portion. Accordingly, the rotation range can be restricted.

The fourth bone member and the third bone member may be constructed by eliminating the rotational axis of the fourth bone member and the third bone member or by integrating the fourth bone member and the third bone member, and a part of the fourth bone member may be configured to be rotatable about an axis perpendicular or nearly perpendicular to the longitudinal axis of the fourth bone member and the third bone member.

The return mechanism may be constituted by, for example, a return member such as a flat spring, a coil spring, or rubber that brings about elasticity to return by using an elastic force. Further, a protrusion or a link mechanism for restricting rotation may be provided on the rotational axis.

For a humanoid hand with five fingers, the second finger is the most preferred example of application of the finger mechanism, but a hand that does not have five fingers, such as a hand (manipulator) constituted by two finger mechanisms, can be considered as an example of application of the finger mechanism of the present invention.

For example, the present invention is a humanoid hand that can be configured to include the finger mechanism described above, wherein the finger mechanism has a second bone member connected to the third bone member, and the second bone member, the third bone member, and the fourth bone member are bent to comfortably come into contact with an object to be held by applying pressure to any of these bone members, or the fourth bone member comes into contact with the object or the thumb so as to face the object or the thumb, to bring about a sufficient contact force to carry out a task such as grasping an object.

Advantageous Effects of Invention

The finger mechanism according to the present invention is capable of performing both delicate tasks and rough tasks such as grasping heavy objects that humans do. In other words, the finger mechanism according to the present invention is capable of mimicking delicate movements of fingers of a person in which the area of contact between fingers changes in accordance with the contact pressure between the tips of the fingers brought into abutment with each other.

Therefore, the tasks that only humans could not perform such as grasping a light, fragile object and the movements with strong and weak brush strokes responding to subtle senses in calligraphy or painting are realized and can be combined with AI.

In addition, the humanoid hand according to the present invention is capable of not only performing the same movements as a human hand, but also smoothly performing both delicate tasks and rough tasks.

BRIEF DESCRIPTION OF DRAWINGS

FIG. 9 is a front view showing a state in which the fourth bone member corresponding to the distal phalanx of the second finger mechanism and the fourth bone member corresponding to the distal phalanx of the thumb mechanism are in strong contact with each other.

DESCRIPTION OF EMBODIMENTS

An embodiment of the present invention is described hereinafter with reference to the drawings, but the present invention is not limited to these.

Figure 1:
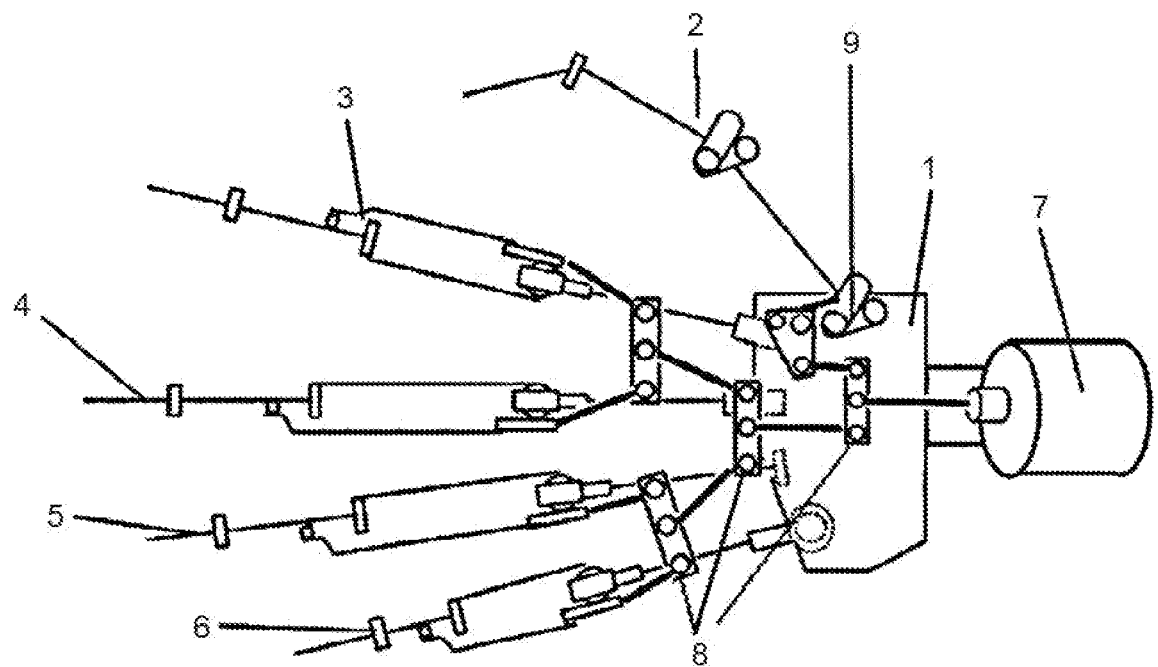
FIG. 1 is an overall view of a humanoid hand according to the present invention.

Examples to which the finger mechanism according to the present invention is applied include a humanoid hand. The one embodiment of this humanoid hand has, as shown in FIG. 1, a palm substrate 1, a thumb mechanism 2, a second finger mechanism 3, a middle finger mechanism 4, a ring finger mechanism 5, and a little finger mechanism 6, and each of these finger mechanisms is operated using a motor 7 as a drive source. In the present embodiment, the drive source is the motor 7, but a drive source other than the motor may be used as long as the drive source can transmit the drive force from the thumb mechanism 2 to the little finger mechanism 6.

A pulling movement using the motor 7 is transmitted to the second finger mechanism 3, the middle finger mechanism 4, the ring finger mechanism 5, and the little finger mechanism 6 via a group of links 8. The pulling movement is transmitted to the thumb mechanism 2 via a group of links 9 branching off from the group of links 8. Although the group of links 8 is illustrated as an example of a means to transmit the power to each of the finger mechanisms, other means can be used as long as the means can transmit the power to each of the finger mechanisms.

In this embodiment, each of the fingers is bent inward by causing the links to perform the pulling movement by driving the motor 7, and each of the fingers is returned to an open state thereof using a return spring or the like.

The second finger mechanism 3, the middle finger mechanism 4, the ring finger mechanism 5, and the little finger mechanism 6 share the same structure. For this reason, the second finger mechanism 3 is described with reference to FIGS. 2 to 5, and the thumb mechanism 2 is described with reference to FIG. 6 and FIG. 7.

The second finger mechanism 3 adopts the finger mechanism of the present invention, and, as shown in FIGS. 2 to 5, has a first bone member 11 corresponding to a metacarpal bone, which has a base end portion connected to the palm substrate 1 via a universal joint (not shown), a second bone member 12 corresponding to the proximal phalanx, which has a base end portion connected rotatably to a tip of the first member 11, a third bone member 13 corresponding to the intermediate phalanx, which has a base end portion connected rotatably to a tip of the second bone member 12, and a fourth bone member 14 corresponding to the distal phalanx, which has a base end portion connected rotatably to a tip of the third member.

The second bone member 12, the third bone member 13, and the fourth bone member 14 are caused to rotate by a link mechanism 20 that is connected to a drive member 19 such as a wire (can be a chain, a rod, or the like) performing a pulling movement by drive of the motor 7.

The link mechanism 20 is constituted by a first link member 21 having a base end portion attached pivotally and rotatably to a connecting axis g1 of the first bone member and the second bone member, a second link member 22 having a base end portion attached pivotally and rotatably to an axis g2 at a tip portion of the first link member 21, and a third link member 23 having a base end portion attached pivotally and rotatably to a connecting axis g3 of the second bone member 12 and the third bone member 13. In the second bone member 12, a section other than the base end portion is bent so as to be positioned on the first bone member 11 side in a thickness direction of the second bone member 12. Similarly, in the third bone member 13, a section other than the base end portion is bent so as to be positioned on the second bone member 12 side in a thickness direction of the third bone member 13. According to this configuration, the second bone member 12 and the third bone member are positioned on a straight line from the first bone member 11 without spreading outward. Furthermore, the third link member 23 and the third bone member 13 are connected by the axis g3 in such a manner that a force is transmitted via the connecting axis, and the third bone member 13 is configured to rotate in response to the rotation of the third link member 23. The drive member 19 is connected to the base end edge portion of the second link member.

Figure 3:
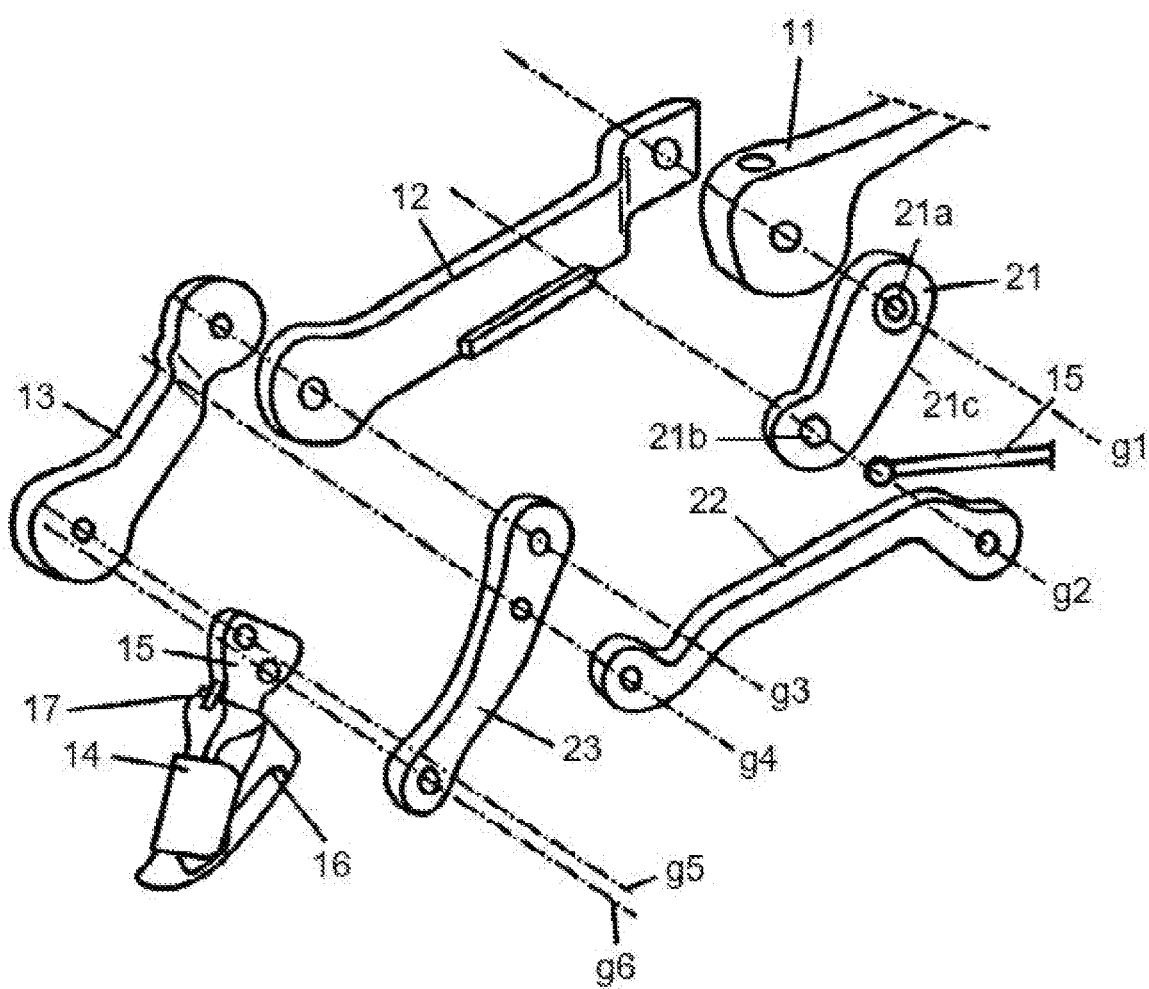
FIG. 3 is an exploded perspective view of the finger mechanism.

The first link member 21 is a plate-like body that is so shaped to be substantially overlapped with the second bone member 12 as viewed laterally, when the first link member 21 is stretched, that is, when the palm is open. However, as shown in FIG. 3, an opening 21a for forming the axis g1 and an opening 21b for forming the axis g2 are provided at positions diverging above (toward the back of the hand) a line parallel to a bottom side 21c. By adopting such a configuration, the conventional triangular rotating plate can be eliminated so that unwanted tension is eliminated, thereby mimicking the shape of an actual human hand.

The second link member 22 has a tip portion attached pivotally to an axis g4 at an intermediate portion of the third link member 23, and the shape of the second link member 22 is curved in a width direction (upward direction in the diagrams) into an elongated S-shape so that, when a strong force acts in an elongation direction, the force is transmitted efficiently to the third link member to stretch the entire finger mechanism.

Moreover, with this curved shape of the second link member 22, even when a strong force acts in a warping direction (upward direction in the diagrams) in the fourth bone member 14, the curving of the second link member 22 can allow the fourth bone member 14 to slightly extend to achieve a straight line. As a result of this extending of the fourth bone member 14, past a singular point (a point where the axis g1, axis g2, and the axis g4 are arranged on the same line), the third bone member 13 and the fourth bone member 14 can rotate in opposite directions (state of dislocation).

In the prior art, since the singular point could not be passed, the finger mechanism would be partially damaged. However, such damage can be avoided by devising the shape of the second link member 22 as described above. Note that the bent shape of the second bone member 12 or the second link member 22 is merely a structure for describing the embodiment of the present invention; thus, these members do not need to be bent to achieve the intended movements thereof.

The third link member 23 is pivotally attached to an axis g6 that is offset downward from a connecting axis g5 between the third bone member 13 and the fourth bone member 14. The positional relationship between these axes g5 and g6 is equivalent to the positional relationship in which the fourth bone member 14 rotates in the direction of closing the finger (the direction of the arrow B shown in FIG. 2) when the third link member 23 rotates counterclockwise (the direction of the arrow A shown in FIG. 2).

In the configuration described above, with the state shown in FIG. 2 (the state in which the finger is stretched) as a standard, the motor 7 is driven in this state, to execute a pulling movement, (to the right in FIG. 2) via the drive member 19 such as a wire.

As a result, the second link member 22 is pulled, whereby a counterclockwise force with respect to the axis g1 as the center is applied to the first link member 21. Since the tip of the second link member 22 pulled toward the base end side is connected to the intermediate portion of the third link member 23, the second bone member 12 to which the base end portion of the third link member 23 is pivotally attached rotates counterclockwise around the axis g1.

Once the second bone member 12 rotates and comes into abutment with an object to be held, the second bone member 12 can no longer be rotated, and further pulling the drive member 19 in this state rotates the third link member 23 counterclockwise about the axis g3.

When the third link member 23 rotates counterclockwise, the third bone member 13 rotates in the same direction, and the fourth bone member 14 rotates counterclockwise as well. As a result, the object to be held is held in such a manner as to be wrapped by the second bone member 12, the third bone member, and the fourth bone member 14.

Figure 4:
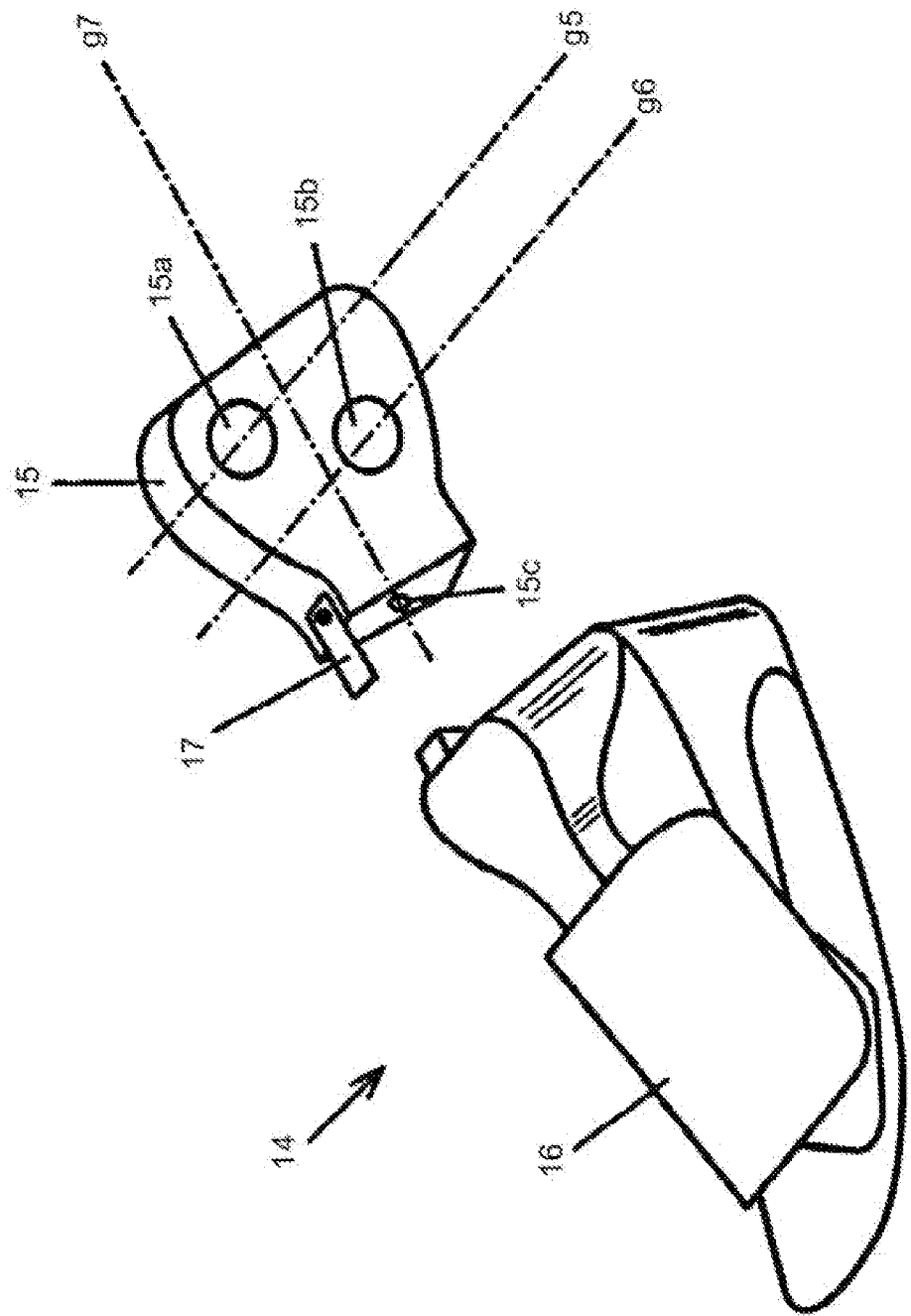
FIG. 4 is an exploded perspective view of a fourth bone member corresponding to a distal phalanx of the second finger mechanism.
Figure 5:
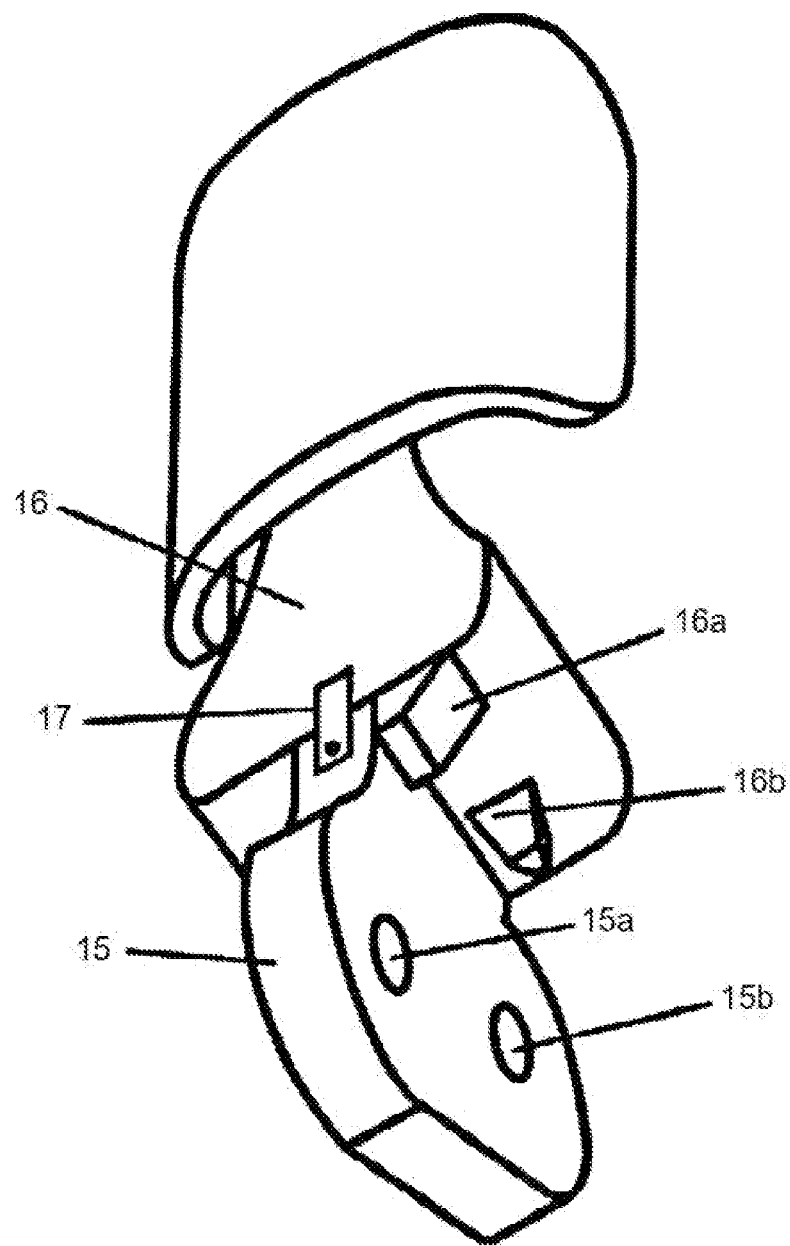
FIG. 5 is a perspective view showing, from behind, the fourth bone member corresponding to the distal phalanx.

The fourth bone member 14 is a member constituting a characteristic part of the finger mechanism of the present invention. As shown in FIG. 4 and FIG. 5, the fourth bone member 14 is composed of a support portion 15 and a nail portion 16. Holes 15a, 15b into which the axes g5, g6 are inserted are formed in the support portion 15, and the fourth bone member 14 is connected to the third bone member 13 via this axis g5. Additionally, an axis hole 15c that supports the nail portion 16 so as to be rotatable about a longitudinal axis g7 is formed. Although not shown particularly, the nail portion 16 is connected to the support portion 15 so as to be rotatable via an axis body provided in this axis hole 15c. Therefore, the nail portion 16, integrated with the support portion 15, is rotatable about the axis g5 which is a rotational axis around which the support portion 15 can rotate with respect to the third bone member 13, and is also rotatable about the axis g7 perpendicular to the axis g5. Moreover, the nail portion 16 is attached to the support portion 15 so as to be rotatable about the axis g7. Therefore, depending on the degree of the force applied to the fourth bone member, only the nail portion 16 can be rotated in a direction that enables easy grasping of the object to be held. Furthermore, stoppers 16a, 16b for restricting the range of rotation described above are formed on the back of the nail portion 16 (FIG. 5). Also, the stoppers 16a, 16b are each made of an elastic member, i.e., a coil spring or rubber. The shapes and sizes of the stoppers 16a, 16b are not particularly limited as long as the stoppers can stop the nail portion 16 from moving. With these stoppers, the nail portion can be prevented from moving more than necessary, so that the object to be held can be held without difficulty.

In addition, on an upper surface of the support portion 15, a base end portion of a flat spring 17 extending to an upper surface of the nail portion 16 is fastened as a return mechanism. The flat spring 17 is in abutment with the nail portion 16 but is not fastened thereto. With the presence of this flat spring 17, when the nail portion 16 is rotated from the state shown in FIG. 5, the nail portion 16 rotates clockwise while twisting the flat spring 17, until the stopper 16b comes into abutment with a side surface of the support portion 15. However, after the rotation of the nail portion 16 is stopped by the stopper, the drive force of the drive member is released, and thereafter the nail portion 16 is returned to the original horizontal position by the returning force of the flat spring 17, that is, to the state shown in FIG. 5.

Furthermore, the joint portion between the fourth bone member 14 and the third bone member 13, that is, the support portion 15 provided with the axis g5, is provided with the axis g6 described above, and is connected to the drive member via the axis g6, and is connected to the third link member 23 that transmits the drive force. Due to such a configuration in which the location of the connection part between the third bone member 13 and the support portion 15 is different from that of the connection part between the third link member and the support portion 15, two-degree-of-freedom with respect to the two directions shown in FIG. 2, i.e., the direction of the arrow A and the direction of the arrow 3, is provided to the support portion 15. By providing two-degree-of-freedom to the support portion 15, the nail portion 16, too, can be operated by taking advantage of two-degree-of-freedom.

The present embodiment has been described above with an example in which the return mechanism is formed by the flat spring functioning as a return member. However, the present invention is not limited to the embodiment, and therefore various elastic members can be used as the return member to constitute the return mechanism. The return mechanism can also be configured by a link mechanism.

Figure 6:
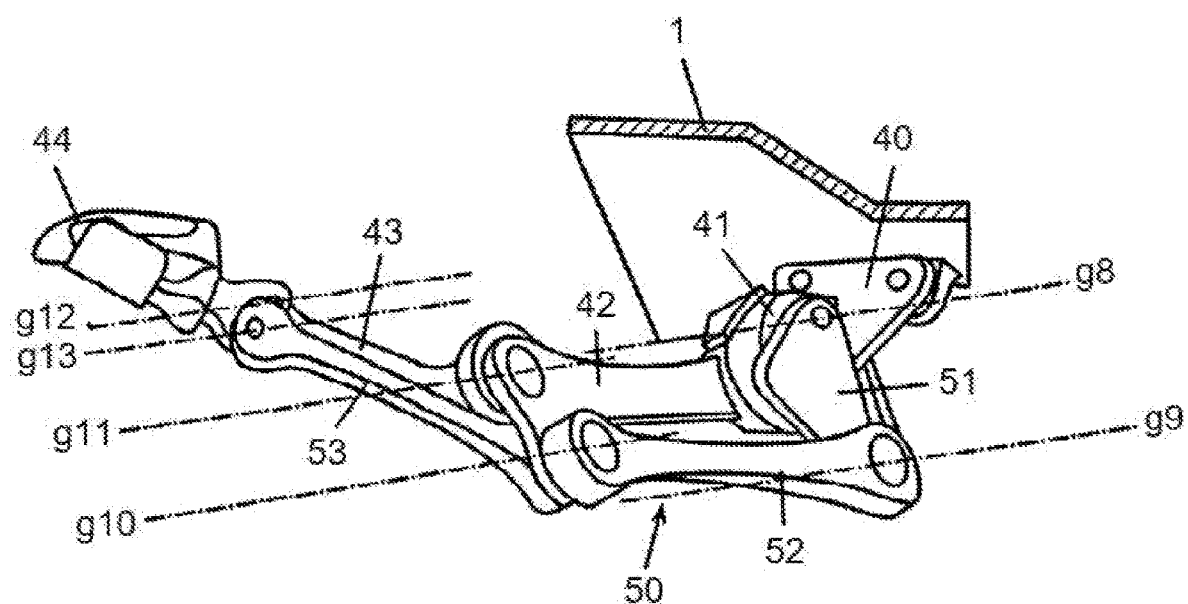
FIG. 6 is a perspective view of a thumb mechanism constituting the humanoid hand.
Figure 7:
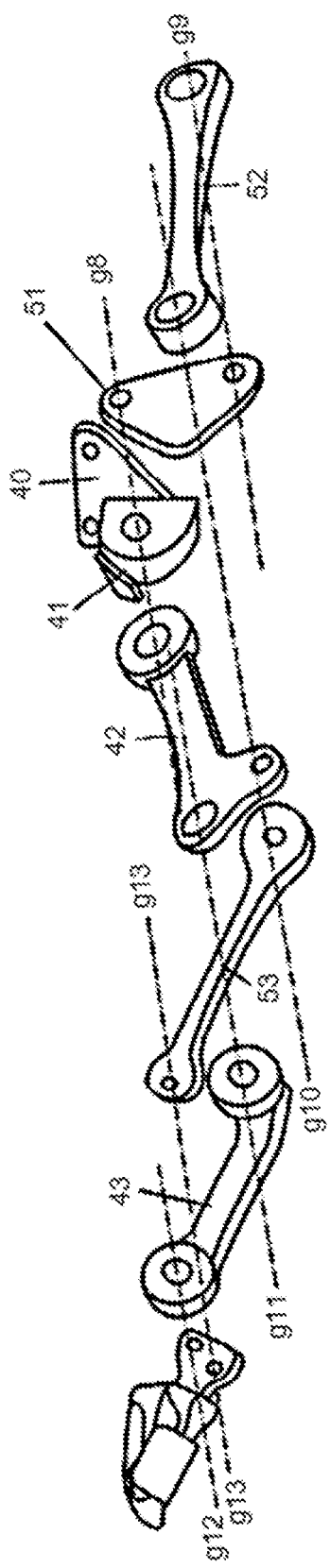
FIG. 7 is an exploded perspective view of the finger mechanism.

As shown in FIGS. 6 and 7, in the thumb mechanism 2, a bracket 40 is attached to a back surface of the palm substrate 1, and a first bone member 41 corresponding to the metacarpal bone is provided in this bracket 40. The thumb mechanism 2 is composed of the first bone member 41, a second bone member 42 corresponding to the proximal phalanx, which has a base end portion connected rotatably to the first member 41, a third bone member 43 corresponding to the intermediate phalanx, which has a base end portion connected rotatably to a tip of the second bone member 42, and a fourth bone member 44 corresponding to the distal phalanx, which has a base end portion coupled rotatably to a tip of the third member 43.

A link mechanism 50 is composed of a triangular first link member 51 that is pivotally and rotatably attached to a connecting axis g8 of the base end portion of the first bone member 41, a second link member 52 that has a base end portion attached pivotally and rotatably to an axis g9 of a tip portion of the first link member 51, and a third link member 53 that has a base end portion attached pivotally and rotatably to a connecting axis g10 of the second link member 52 and the third bone member 43. Although particularly not shown, the drive member is connected to the first link member 51 so as to transmit the drive force from the motor 7.

The axis 10 is offset from a pivot axis g11 of the second bone member 42 and the third bone member 43. The third link member 53 having the base end portion supported by the axis 10 is pivotally attached to an axis g13 that is offset from a connecting axis g12 of the third bone member 43 and the fourth bone member 44. The positional relationship between these axes g13 and g14 is equivalent to the positional relationship in which the third link member 53 rotates in the direction of closing the finger when a force in a pressing direction acts on the third link member 53.

In the configuration described above, with the state shown in FIG. 2 (the state in which the finger is stretched) as a standard, the motor 7 is driven in this state to execute a pulling movement (to the right in FIG. 2) via the drive member 19 such as a wire. As a result, a counterclockwise force around the axis g1 is applied to the first link member 21, thereby pulling the second link member 22. Since the tip of the second link member 22 is connected to the intermediate portion of the third link member 23, the second bone member 12 to which the base end portion of the third link member 23 is pivotally attached rotates counterclockwise around the axis g1, causing the second link member 22 to perform the pulling movement. Consequently, the third bone member 13 rotates counterclockwise, and the third link member 23 rotates, whereby the fourth bone member 14 rotates counterclockwise.

In the thumb mechanism 2 as well, by rotating the first link member 51 clockwise about the axis g8 by driving the motor 7, the second link member 52 performs a pressing movement, and this pressing movement causes the third link member 53 to perform a pressing movement. This pressing movement causes the thumb mechanism 2 to perform a closing movement.

Figure 2:
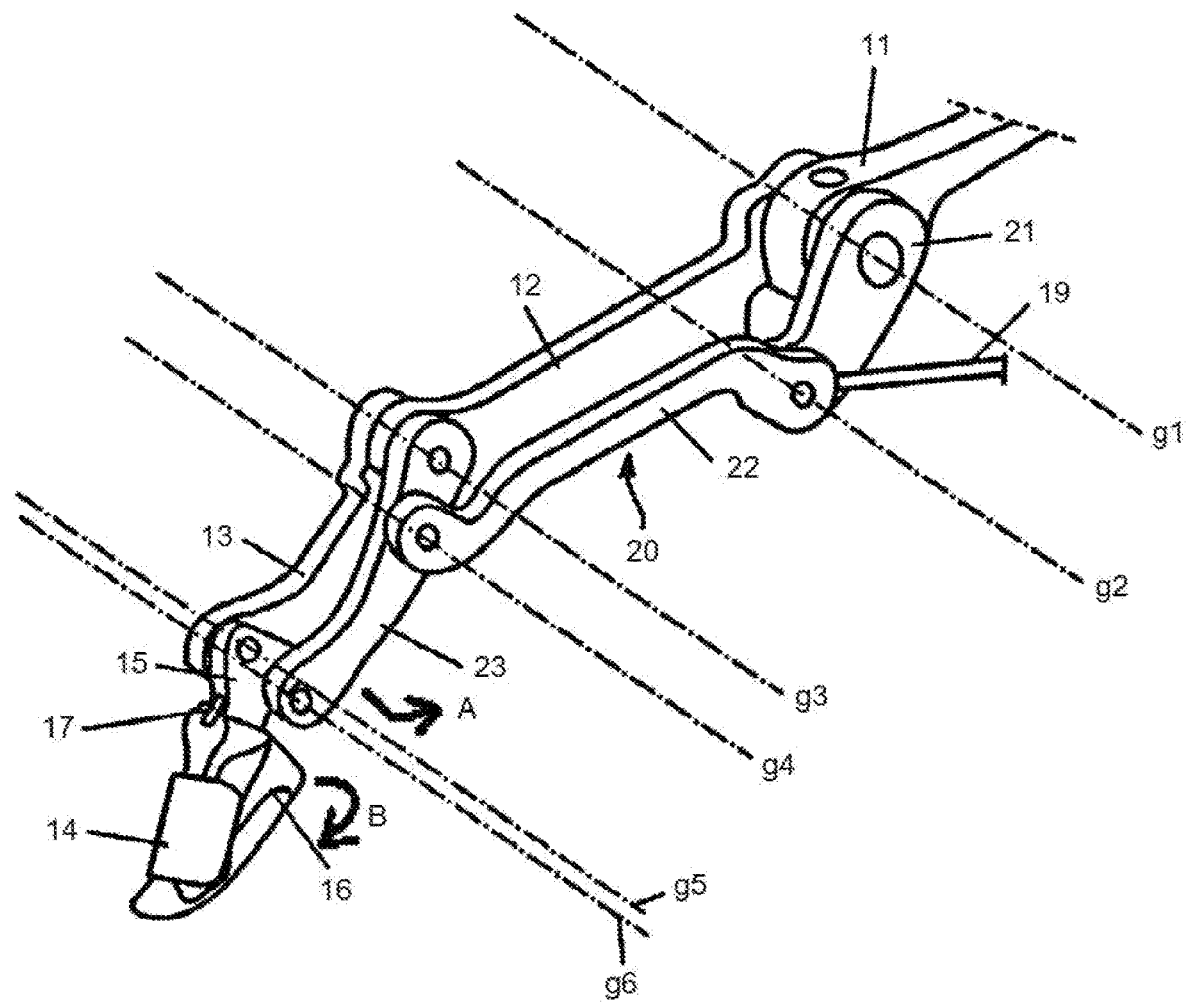
FIG. 2 is a perspective view of a second finger mechanism constituting the humanoid hand.

The closing movements of the thumb mechanism 2 and the second finger mechanism 3 cause the nail portion 16 of the second finger mechanism 3 to be pulled by the third link member 23, causing the nail portion 16 to rotate integrally with the support portion 15 not only in the direction of the arrow A shown in FIG. 2 but also in the direction of the arrow B. Consequently, as shown in FIG. 8, the fourth bone member 14 of the second finger mechanism 3 becomes inclined with respect to the fourth bone member 44 of the thumb mechanism 2, and while the fourth bone member 44 of the thumb mechanism 2 and the fourth bone member 14 of the second finger mechanism 3 are in gentle contact with each other, the parts corresponding to the fingertips are in partial contact with each other, as shown in FIG. 8.

In a case where surfaces of the fourth bone members of the thumb mechanism 2 and the second finger mechanism 3 are covered with an elastic member such as urethane, the surfaces of the fourth bone members become slightly squished. Thus, although the fourth bone members are not in point contact with each other, the area of contact therebetween is small, thus achieving grasping of the object to be held with the tips of the respective finger mechanisms, with little force.

By increasing the contact pressure between the fourth bone member 14 and the fourth bone member 44 by further driving the motor 7 in the foregoing state, the nail portion 16 constituting the fourth bone member 14 rotates about the axis g7 while deforming the flat spring 17 so as to follow the fourth bone member 44. As a result, the nail portion 16 and the fourth bone member 44 of the thumb mechanism 2 becomes almost parallel to each other as shown in FIG. 9, increasing the area of contact therebetween.

Figure 8:
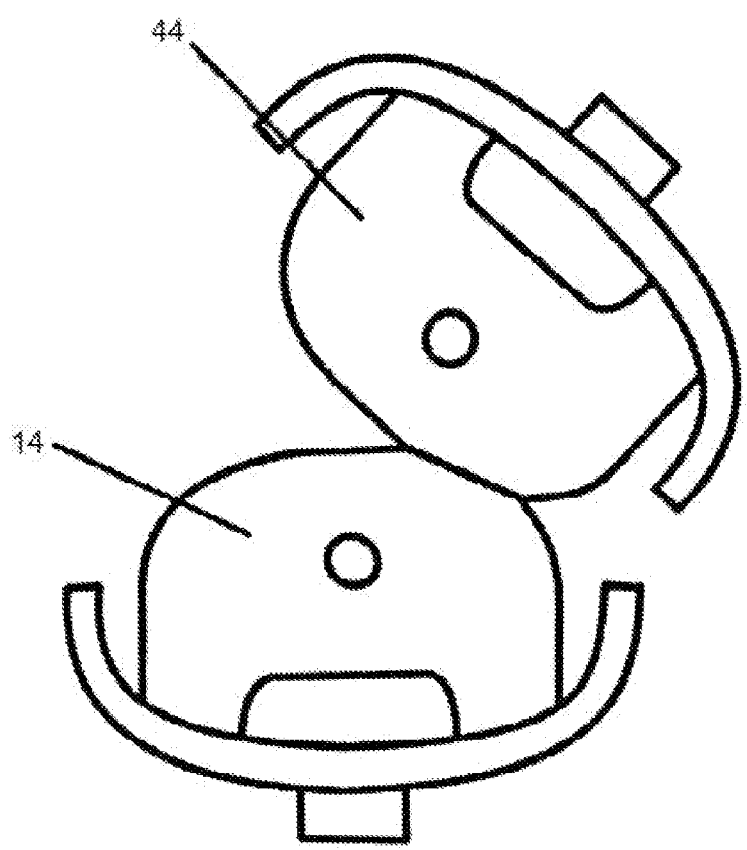
FIG. 8 is a front view showing a state in which the fourth bone member corresponding to the distal phalanx of the second finger mechanism and a fourth bone member corresponding to a distal phalanx of the thumb mechanism are in gentle contact with each other.

The states shown in FIG. 8 and FIG. 9 can be repeated by reversing the rotation of the motor 7.

INDUSTRIAL APPLICABILITY

Although the embodiment has described a humanoid hand having five fingers, the present invention can be applied to a hand having two or more fingers because the present invention is characterized in that the area of contact between two fingertips changes in accordance with the contact pressure therebetween.

The humanoid hand according to the present invention can be used both for industrial purposes and as a prosthetic hand.

REFERENCE SIGNS LIST

1 Palm substrate
2 Thumb mechanism
3 Second finger mechanism
4 Middle finger mechanism
5 Ring finger mechanism
6 Little finger mechanism
7 Motor (stepping motor)
8, 9 Group of links
11 First bone member
12 Second bone member
13 Third bone member
14 Fourth bone member
15 Support portion
15a, 15b, 15c Axis hole
16 Nail portion
16a, 16b Stopper
17 Flat spring
19 Drive member
20 Link mechanism
21 First link member
22 Second link member
23 Third link member
40 Bracket
41 First bone member
42 Second bone member
43 Third bone member
44 Fourth bone member
50 Link mechanism
51 First link member
52 Second link member
53 Third link member
g1, g2, g3, g4, g5, g6, g7, g8, g9, g10, g11, g12, g13 Axis

The invention claimed is:

1. A finger mechanism comprising:
a bone member;
a support portion rotatably connected to the bone member;
a nail portion rotatably supported by the support portion, such that the nail portion is rotatable about a first axis with respect to the support portion, the first axis being perpendicular or nearly perpendicular to a second axis about which the support portion is rotatable with respect to the bone member; and
a return mechanism provided between the support portion and the nail portion, wherein
the nail portion is rotatable depending on a contact pressure generated due to contact between the nail portion and an object, and
the return mechanism is configured to return the rotated nail portion to a reference position.

2. The finger mechanism according to claim 1, wherein
the bone member and a link member for transmitting a drive force are connected to the support portion, and
a location of a connection part between the bone member and the support portion is different from a location of a connection part between the link member and the support portion.

3. The finger mechanism according to claim 1, wherein either the support portion or the nail portion is provided with a stopper for restricting a rotation range of the nail portion.

4. The finger mechanism according to claim 1, wherein the return mechanism is made of an elastic body.

5. The finger mechanism according to claim 4, wherein the elastic body is at least one of a flat spring, a coil spring or rubber.

6. A hand comprising the finger mechanism according to claim 1.

7. The hand according to claim 6, further comprising a drive source configured to transmit a drive force to the finger mechanism.

8. The finger mechanism according to claim 1, wherein the bone member is corresponding to an intermediate phalanx, and a further bone member corresponding to a distal phalanx is constituted by the nail portion and the support portion.

9. A hand comprising the finger mechanism according to claim 8, wherein the finger mechanism further has a still further bone member connected to the bone member corresponding to the intermediate phalanx, and the bone members are bent to come into contact with the object to be held by applying pressure to any of the bone members, to bring about a sufficient contact force to carry out a task for grasping the object.

10. The hand according to claim 9, wherein
the bone member corresponding to the intermediate phalanx and a link member for transmitting a drive force are connected to the support portion,
the finger mechanism further comprises a further link member that includes a tip portion attached pivotally to an axis at an intermediate portion of the link member connected to the support portion, and
the further link member is curved in a width direction for transmitting a force efficiently to the link member connected to the support portion to stretch the entire finger mechanism.

11. A hand comprising the finger mechanism according to claim 8, wherein the finger mechanism further has a still further bone member connected to the bone member corresponding to the intermediate phalanx, and the further bone member corresponding to the distal phalanx comes into contact with the object so as to face the object, to bring about a sufficient contact force to carry out a task for grasping the object.

12. The finger mechanism according to claim 1, wherein the nail potion rotates in order to increase an area that is in contact with the object as the contact pressure increases.

13. The finger mechanism according to claim 1, wherein the object is a nail potion of another finger mechanism.

14. The finger mechanism according to claim 1, wherein an angle between the first axis about which the nail portion is rotated and the second axis about which the support portion is rotatable with respect to the bone member is in a range from 80° to 100°.

15. The finger mechanism according to claim 1, wherein the reference position represents a position of the nail portion when the nail portion does not contact with the object.

16. A finger mechanism, wherein a bone member corresponding to a distal phalanx out of bone members of the finger mechanism is constituted by a support portion and a nail portion,
the support portion is connected to a bone member corresponding to an intermediate phalanx,
the nail portion is rotatable about a first axis with respect to the support portion, the first axis being perpendicular or nearly perpendicular to a second axis about which the support portion is rotatable with respect to the bone member corresponding to the intermediate phalanx,
between the support portion and the nail portion, a return mechanism for returning the rotated nail portion to a reference position is provided, and
the nail portion is rotatable depending on a contact pressure generated due to contact between the nail portion and an object.

17. The finger mechanism according to claim 16, wherein either the support portion or the nail portion is provided with a stopper for restricting a rotation range of the nail portion.

18. A hand comprising the finger mechanism according to claim 16.

19. The finger mechanism according to claim 16, wherein the nail potion rotates in order to increase an area that is in contact with the object as the contact pressure increases.

20. The finger mechanism according to claim 16, wherein the reference position represents a position of the nail portion when the nail portion does not contact with the object.

* * * * *